United States Patent [19]

Shinohara et al.

[11] Patent Number: 5,084,591
[45] Date of Patent: Jan. 28, 1992

[54] METHOD FOR THE PREPARATION OF CYCLOPENTYL TRICHLOROSILANE

[75] Inventors: Toshio Shinohara; Motoaki Iwabuchi, both of Gunma, Japan

[73] Assignee: Shin-Etsu Chemical Co., Ltd., Tokyo, Japan

[21] Appl. No.: 710,870

[22] Filed: Jun. 6, 1991

[30] Foreign Application Priority Data

Jun. 7, 1990 [JP] Japan ................... 2-149338

[51] Int. Cl.⁵ ............................... C07F 7/08
[52] U.S. Cl. .................................. 556/479
[58] Field of Search ........................ 556/479

[56] References Cited

U.S. PATENT DOCUMENTS 2,823,218  2/1958  Speier et al. ............ 556/479 X
4,883,569  11/1989  Endo et al. ............. 556/479 X

FOREIGN PATENT DOCUMENTS 64-83089  3/1989  Japan ................... 556/479

*Primary Examiner*—Paul F. Shaver
*Attorney, Agent, or Firm*—Millen, White & Zelano

[57] ABSTRACT

Cyclopentyl trichlorosilane can be efficiently prepared by the hydrosiliaton reaction of trichlorosilane and cyclopentene which can proceed only to a very low extent by the use of conventional platinum catalysts effective in other hydrosilation reactions. Thus, an equimolar mixture of the reactants is heated in the presence of a chlorine-deficient chloroplatinic acid catalyst of a specified chlorine:platinum atomic ratio at a temperature higher than the boiling point of the mixture under normal pressure in a pressurizable vessel so that the desired product can be obtained in a yield of 90% of the theoretical value or higher.

4 Claims, No Drawings

METHOD FOR THE PREPARATION OF CYCLOPENTYL TRICHLOROSILANE

BACKGROUND OF THE INVENTION

The present invention relates to a method for the synthetic preparation of cyclopentyl trichlorosilane or, more particularly, to a method for the preparation of cyclopentyl trichlorosilane from trichlorosilane and cyclopentene by the hydrosilation reaction.

Cyclopentyl trichlorosilane is a compound having usefulness as an intermediate in the synthetic preparation of various kinds of organosilicon compounds having two or three cycloalkyl groups in a molecule. Since cyclopentyl-containing organosilicon compounds have a refractive index intermediate between those of methyl- and phenyl-containing organosilicon compounds, an advantage is expected in matching of the refractive indices when a transparent silicon composition is desired. Further, the bulkiness of the cyclopentyl group promisingly indicates the usefulness of cyclopentyl-containing silane compounds as a silylating agent in various organic synthesis for which tert-butyl dimethyl chlorosilane is the most conventional. Several methods are known in the prior art for the preparation of this compound. For example, the so-called "direct method" proposed by E. G. Rochow is also applicable to the preparation of this silane compound in which metallic silicon and cyclopentyl chloride are reacted in the presence of a copper catalyst. Alternatively, it can be synthesized by the reaction of a cyclopentyl magnesium halide as a Grignard reagent with tetrachlorosilane.

The above mentioned "direct method" is not advantageous when the organosilane compound to be prepared is cyclopentyl trichlorosilane because by-products are formed in large amounts so that great difficulties are encountered in the isolation and purification of cyclopentyl trichlorosilane. The Grignard method has an economical disadvantage as an industrial method due to the expensiveness of the Grignard reagent in addition to the problem of troublesomeness and danger of fire or explosion accompanying the use of a very inflammable organic solvent such as ether. Moreover, the productivity of the Grignard method cannot be high enough due to the formation of a large amount of a magnesium halide as the by-product which must be removed from the reaction mixture. Further, the Grignard reagent, i.e. cyclopentyl magnesium halide, is highly susceptible to oxidation by oxygen in the atmospheric air to be converted into cyclopentyloxy magnesium halide from which cyclopentyloxy trichlorosilane is formed as the product of the Grignard reaction while this compound can hardly be separated from cyclopentyl trichlorosilane, for example, by distillation because these two compounds have physical properties very close to each other.

It would be a speculatively possible way that cyclopentyl trichlorosilane could be prepared by the hydrosilation reaction between trichlorosilane and cyclopentene in the presence of a platinum compound such as chloroplatinic acid as a catalyst according to a procedure well known in the hydrosilation between a silicon compound having a silicon-bonded hydrogen atom and a linear alkenyl compound. Different from other cycloalkene compounds such as cyclohexene of a 6-membered ring, nevertheless, no report is found in the literatures for the hydrosilation reaction of cyclopentene with trichlorosilane. This is presumably due to the low reactivity of cyclopentene even by the catalytic promotion of the reaction by conventional platinum catalysts.

SUMMARY OF THE INVENTION

The present invention accordingly has an object to provide a novel and efficient method for the synthetic preparation of cyclopentyl trichlorosilane by the hydrosilation reaction between trichlorosilane and cyclopentene without the problems and disadvantages in the above described prior art methods such as the "direct method" and the Grignard method.

Thus, the method of the present invention for the preparation of cyclopentyl trichlorosilane comprises the steps of:

(a) mixing trichlorosilane, cyclopentene and a chlorine-deficient chloroplatinic acid catalyst, of which the atomic ratio of chlorine to platinum is in the range from 0.001 to 0.1, to form a reaction mixture; and (b) heating the reaction mixture at a temperature higher by at least 1° C. than the boiling point of the reaction mixture under normal pressure or, preferably, in the range from 50° to 80° C.

DETAILED DESCRIPTION OF THE PREFERRED EMBODIMENTS

As is understood from the above description, the most characteristic feature of the inventive method for the hydrosilation reaction consists in the use of a very specific platinum catalyst and in the specific reaction conditions relative to the temperature.

While the amounts of trichlorosilane and cyclopentene pertaining to the hydrosilation reaction are equimolar, the molar ratio of cyclopentene to trichlorosilane in the reaction mixture should be in the range from 0.6 to 1.5 or, preferably, from 0.9 to 1.1 from the standpoint of productivity of the process. When one of the reactants is used in an excessive amount over equimolar, a portion of the reactant remains unreacted in the reaction mixture after completion of the reaction as a matter of course and must be removed from the mixture to isolate the cyclopentyl trichlorosilane as the product. When the reaction is performed under appropriately selected conditions according to the inventive method, the reaction proceeds almost quantitatively with formation of very small amounts of by-products.

Different from the platinum catalysts conventionally used in the hydrosilation reaction, the platinum catalyst used in the inventive method is a chlorine-deficient chloroplatinic acid catalyst, of which the atomic ratio of chlorine to platinum is in the range from 0.001 to 0.1. When conventional chloroplatinic acid or chloroplatinous acid, in which the atomic ratio of chlorine to platinum is 6 or 4, respectively, is used as such as the catalyst for the hydrosilation reaction between trichlorosilane and cyclopentene, the extent of the reaction can rarely exceed 20%. It was discovered quite unexpectedly that the hydrosilation reaction could proceed almost to completeness when the catalyst was a chlorine-deficient chloroplatinic acid catalyst of which the atomic ratio of chlorine to platinum was in the above specific range. Such a chlorine-deficient chloroplatinic acid catalyst can be prepared by the treatment of chloroplatinic acid with sodium hydrogencarbonate and an organosiloxane compound having a silicon-bonded vinyl group in a molecule according to the disclosure in Japanese Patent Publication 47-23679. The chlorine-deficient chloroplatinic acid catalyst is prepared usually in the form of a solution in a solvent such as lower aliphatic alcohols, e.g., ethyl, n-butyl and 2-ethylhexyl alcohols, aromatic hydrocarbon solvents, e.g., toluene, and silicone fluids in a concentration of 0.01 to 10% by weight as platinum. The amount of the platinum catalyst added to the reaction mixture is usually in the range from 1 to 1000 ppm by weight or, preferably, in the range from 10 to 500 ppm by weight as platinum based on the total amount of trichlorosilane and cyclopentene.

The reaction mixture prepared by mixing trichlorosilane, cyclopentene and the platinum catalyst is then heated under an atmosphere of an inert gas at a temperature higher by at least 1° C. than the boiling point of the mixture under normal pressure. In view of the boiling point 31.5° C. of trichlorosilane, the reaction temperature is preferably in the range from 50° to 80° C. Needless to say, the reaction must be performed in a closed pressurizable vessel which should withstand the pressure spontaneously produced by heating the reaction mixture in the above mentioned reaction temperature. The pressure is usually in the range from 2 to 10 kg/cm$^2$G. The reaction is complete under the above mentioned conditions usually within 50 hours or, in most cases, within 30 hours. When the reaction temperature is too low, the velocity of the reaction cannot be high enough. On the other hand, no further advantages can be obtained by further increasing the reaction temperature to exceed the above mentioned upper limit due to the instability of the catalyst at such a high temperature rather with a disadvantage due to an increase in the amounts of by-products if not to mention the problem in the pressure-resistance of the reaction vessel.

In the following, the method of the present invention is described in more detail by way of examples.

EXAMPLE 1

The atomic ratio of chlorine to platinum was 0.05 in the chlorine-deficient chloroplatinic acid catalyst, referred to as the catalyst I hereinbelow, used in this example, which was prepared by treating chloroplatinic acid hexahydrate with sodium hydrogencarbonate according to the disclosure in Japanese Patent Publication 47-23679 and was in the form of a solution in toluene in a concentration of 0.5% by weight as platinum.

Into an autoclave of 2-liter capacity were introduced 141 g (1.04 moles) of trichlorosilane, 71 g (1.04 moles) of cyclopentene and 4.1 g of the catalyst I mentioned above corresponding to 97 ppm by weight as platinum based on the total amount of trichlorosilane and cyclopentene to form a reaction mixture, which was heated at 65° to 75° C. for 24 hours under a spontaneously produced pressure of about 4 kg/cm$^2$G. Small portions of the reaction mixture were periodically taken out of the autoclave and analyzed by the gas chromatography to monitor progress of the reaction. More than 99% of the starting reactants had been reacted at the end of the reaction time of 24 hours. The reaction mixture after cooling to room temperature was taken out of the autoclave and distilled under normal pressure to remove the unreacted starting materials and other volatile constituents. The residue after this stripping treatment was subjected to distillation under reduced pressure to give 199 g of a fraction boiling at 70° C. under a pressure of 18 mmHg, which could be identified to be the desired cyclopentyl trichlorosilane. The molar yield of the product was 0.94 mole corresponding to 90% of the theoretical value after isolation.

EXAMPLE 2

The experiment was conducted in substantially the same manner as in Example 1 by preparing a reaction mixture from 19.5 g (0.144 mole) of trichlorosilane, 9.9 g (0.146 mole) of cyclopentene and 0.14 g of the catalyst I corresponding to 238 ppm by weight as platinum based on the total amount of trichlorosilane and cyclopentene and heating the mixture in a polytetrafluoroethylene-made pressure-resistant vessel at 60° C. for 26 hours under a spontaneously produced pressure of 3 kg/cm$^2$G. About 97% of the starting reactants had been reacted at the end of the reaction time as determined by the gas chromatographic analysis. Treatment of the reaction mixture after the reaction was performed in the same manner as in Example 1 to give cyclopentyl trichlorosilane in a yield of 91% as isolated based on the theoretical value.

EXAMPLE 3

The atomic ratio of chlorine to platinum was 0.05 in the chlorine-deficient chloroplatinic acid catalyst, referred to as the catalyst II hereinbelow, used in this example, which was prepared by treating chloroplatinic acid hexahydrate with sodium hydrogen-carbonate according to the disclosure in Japanese Patent Publication 47-23679 and was in the form of a solution in ethyl alcohol in a concentration of 3.0% by weight as platinum.

The experiment was conducted in substantially the same manner as in Example 1 by preparing a reaction mixture from 20.5 g (0.151 mole) of trichlorosilane, 9.7 g (0.143 mole) of cyclopentene and 0.09 g of the catalyst II corresponding to 88 ppm by weight as platinum based on the total amount of trichlorosilane and cyclopentene and heating the mixture in a polytetrafluoroethylene-made pressure-resistant vessel at 80° C. for 18 hours under a spontaneously produced pressure of 5 kg/cm$^2$G. About 97% of the starting reactants had been reacted at the end of the reaction time as determined by the gas chromatographic analysis. Treatment of the reaction mixture after the reaction was performed in the same manner as in Example 1 to give cyclopentyl trichlorisilane in a yield of 90% as isolated based on the theoretical value.

COMPARATIVE EXAMPLE 1

The reaction was performed by agitating the reaction mixture, which was prepared from 19.1 g (0.141 mole) of trichlorosilane, 9.2 g (0.135 mole) of cyclopentene and 0.13 g of the catalyst I corresponding to 23 ppm by weight as platinum based on the total amount of trichlorosilane and cyclopentene, in a glass flask at 30° C. for 22 hours under normal pressure. Only about 22% of the starting reactants had been reacted after the end of this reaction time as determined by the gas chromatographic analysis. Treatment of the reaction mixture after the reaction was performed in the same manner as in Example 1 to give 5.2 g (0.0256 mole) of cyclopentyl trichlorosilane in a yield of 19% as isolated based on the theoretical value.

COMPARATIVE EXAMPLE 2

The atomic ratio of chlorine to platinum was 3.5 in the chlorine-deficient chloroplatinic acid catalyst, referred to as the catalyst III hereinbelow, used in this comparative example, which was prepared by treating chloroplatinic acid hexahydrate with sodium hydrogencarbonate according to the disclosure in Japanese Patent Publication 47-23679 and was in the form of a solution in 2-ethylhexyl alcohol in a concentration of 2% by weight as platinum.

Into a pressure-resistant polytetrafluoroethylene vessel were introduced 20.5 g (0.151 mole) of trichlorosilane, 9.7 g (0.143 mole) of cyclopentene and 0.14 g of the catalyst III corresponding to 93 ppm by weight as platinum based on the total amount of trichlorosilane and cyclopentene to form a reaction mixture which was heated at 80° C. for 22 hours in the closed vessel to effect the reaction. The pressure inside the vessel was about 5 kg/cm$^2$G throughout the reaction time. The reaction mixture after the reaction time was analyzed by the gas chromatography for the content of cyclopentyl trichlorosilane to find that the reaction had proceeded only to 22% of the theoretical yield.

What is claimed is:

1. A method for the preparation of cyclopentyl trichlorosilane which comprises the steps of:

(a) mixing trichlorosilane, cyclopentene and a chlorine-deficient chloroplatinic acid catalyst, of which the atomic ratio of chlorine to platinum is in the range from 0.001 to 0.1, to form a reaction mixture; and (b) heating the reaction mixture at a temperature higher by at least 1° C. than the boiling point of the reaction mixture under normal pressure.

2. The method for the preparation of cyclopentyl trichlorosilane as claimed in claim 1 in which the temperature in step (b) is in the range from 50° to 80° C.

3. The method for the preparation of cyclopentyl trichlorosilane as claimed in claim 1 in which the molar ratio of the amount of cyclopentene to the amount of trichlorosilane is in the range from 0.6 to 1.5.

4. The method for the preparation of cyclopentyl trichlorosilane as claimed in claim 1 in which the amount of the catalyst is in the range from 1 to 1000 ppm by weight as platinum based on the total amount of trichlorosilane and cyclopentene.

* * * * *